(12) United States Patent
Boyle et al.

(10) Patent No.: US 8,905,946 B2
(45) Date of Patent: Dec. 9, 2014

(54) NICKEL—TITANIUM CORE GUIDE WIRE

(71) Applicant: Abbott Cardiovascular Systems Inc., Santa Clara, CA (US)

(72) Inventors: William J. Boyle, Fallbrook, CA (US); Wayne E. Cornish, Fallbrook, CA (US); Raleigh A. Purtzer, Winchester, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/209,243

(22) Filed: Mar. 13, 2014

(65) Prior Publication Data

US 2014/0190230 A1     Jul. 10, 2014

Related U.S. Application Data

(62) Division of application No. 13/954,139, filed on Jul. 30, 2013, now Pat. No. 8,679,035, which is a division of application No. 12/914,049, filed on Oct. 28, 2010, now Pat. No. 8,500,658.

(51) Int. Cl.
*A61B 5/00*     (2006.01)

(52) U.S. Cl.
USPC ........................................................ 600/585

(58) Field of Classification Search
USPC ............................................ 600/585; 29/33 F
See application file for complete search history.

(56) References Cited

U.S. PATENT DOCUMENTS

| | | | |
|---|---|---|---|
| 5,904,657 A | 5/1999 | Unsworth et al. | |
| 6,168,571 B1 | 1/2001 | Solar et al. | |
| 6,241,744 B1 * | 6/2001 | Imran et al. | 606/159 |
| 6,375,628 B1 * | 4/2002 | Zadno-Azizi et al. | 600/585 |
| 6,620,126 B2 | 9/2003 | Unsworth et al. | |
| 7,468,045 B2 * | 12/2008 | Nuss | 600/585 |
| 7,611,479 B2 * | 11/2009 | Cragg et al. | 604/13 |
| 7,625,352 B1 * | 12/2009 | Ashby et al. | 604/15 |
| 7,632,361 B2 | 12/2009 | Johnson et al. | |
| 8,500,787 B2 * | 8/2013 | Simpson et al. | 623/1.11 |

* cited by examiner

*Primary Examiner* — Max Hindenburg
(74) *Attorney, Agent, or Firm* — Fulwider Patton LLP

(57) ABSTRACT

A guide wire for use in a medical procedure having a shapeable tip integral with and made from the distal end of a superelastic nitinol distal section of the guide wire, wherein the shapeable tip can be finger kinked. Such a guide wire includes an elongated core made from a superelastic nitinol alloy at the distal end, the distal end of the elongated core having a tapered section leading to a shapeable distal tip. The shapeable tip is an extension of the distal end of the nitinol distal section, and includes permanent strain hardening from at least two different radial directions imparting crystallographic texture in the radial directions that eliminate superelasticity so that permanent deformation can be achieved with finger pressure.

7 Claims, 3 Drawing Sheets

NICKEL—TITANIUM CORE GUIDE WIRE

This application is a division of co-pending U.S. Ser. No. 13/954,139 filed Jul. 30, 2013, which is a division of U.S. Ser. No. 12/914,049 filed Oct. 28, 2010, now U.S. Pat. No. 8,500,658, the entire contents of which are hereby incorporated by reference.

BACKGROUND

This invention relates to the field of guide wires for advancing intraluminal devices such as stent delivery catheters, balloon dilatation catheters, atherectomy catheters and the like within a patient's body, such as within a patient's vasculature.

In a typical percutaneous procedure in a patient's coronary system, a guiding catheter having a preformed distal tip is percutaneously introduced into a patient's peripheral artery, e.g., femoral, radial or brachial artery, by means of a conventional Seldinger technique and advanced therein until the distal tip of the guiding catheter is seated in the ostium of a desired coronary artery. There are two basic techniques for advancing a guide wire into the desired location within the patient's coronary anatomy, the first is a preload technique which is used primarily for over-the-wire (OTW) devices, and the second is the bare wire technique which is used primarily for rail type systems.

With the preload technique, a guide wire is positioned within an inner lumen of an OTW device such as a dilatation catheter or stent delivery catheter with the distal tip of the guide wire just proximal to the distal tip of the catheter and then both are advanced through the guiding catheter to the distal end thereof. The guide wire is first advanced out of the distal end of the guiding catheter into the patient's coronary vasculature until the distal end of the guide wire crosses the arterial location where the interventional procedure is to be performed, e.g., a lesion to be dilated or a dilated region where a stent is to be deployed.

The catheter, which is slidably mounted onto the guide wire, is advanced out of the guiding catheter into the patient's coronary anatomy over the previously introduced guide wire until the operative portion of the intravascular device, e.g., the balloon of a dilatation or a stent delivery catheter, is positioned across the arterial location. Once the catheter is in position with the operative means located within the desired arterial location, the interventional procedure is performed. The catheter can then be removed from the patient over the guide wire. Usually, the guide wire is left in place for a period of time after the procedure is completed to ensure re-access to the arterial location if it is necessary. For example, in the event of arterial blockage due to dissected lining collapse, a rapid exchange type perfusion balloon catheter such as described and claimed in U.S. Pat. No. 5,516,336 (McInnes et al.), can be advanced over the in-place guide wire so that the balloon can be inflated to open up the arterial passageway and allow blood to perfuse through the distal section of the catheter to a distal location until the dissection is reattached to the arterial wall by natural healing.

With the bare wire technique, the guide wire is first advanced by itself through the guiding catheter until the distal tip of the guide wire extends beyond the arterial location where the procedure is to be performed. Then a rail type catheter, such as described in U.S. Pat. No. 5,061,273 (Yock) and the previously discussed McInnes et al. which are incorporated herein by reference, is mounted onto the proximal portion of the guide wire that extends out of the proximal end of the guiding catheter outside of the patient. The catheter is advanced over the guide wire, while the position of the guide wire is fixed, until the operative means on the rail type catheter is disposed within the arterial location where the procedure is to be performed. After the procedure the intravascular device may be withdrawn from the patient over the guide wire or the guide wire advanced further within the coronary anatomy for an additional procedure.

Conventional guide wires for angioplasty, stent delivery, atherectomy and other vascular procedures usually comprise an elongated core member with one or more tapered sections near the distal end thereof and a flexible body such as a helical coil or a tubular body of polymeric material disposed about the distal portion of the core member. A shapeable member, which may be the distal extremity of the core member or a separate shaping ribbon secured to the distal extremity of the core member, extends through the flexible body and is secured to the distal end of the flexible body by soldering, brazing or welding, which forms a rounded distal tip. Torquing means are provided on the proximal end of the core member to rotate, and thereby steer, the guide wire while it is being advanced through a patient's vascular system.

Further details of guide wires, and devices associated therewith for various interventional procedures can be found in U.S. Pat. No. 4,748,986 (Morrison et al.); U.S. Pat. No. 4,538,622 (Samson et al.): U.S. Pat. No. 5,135,503 (Abrams); U.S. Pat. No. 5,341,818 (Abrams et al.); U.S. Pat. No. 5,345,945 (Hodgson, et al.); and U.S. Pat. No. 5,636,641 (Fariabi); all of which are hereby incorporated herein in their entirety by reference thereto.

One of the challenges with conventional guide wires is that the distal portion is typically made from a superelastic or pseudoelastic nickel-titanium (NiTi) alloy, and due to the highly elastic behavior, the cardiologist may have issues with creating a permanent kink or bend at the distal end since the resilience of the material returns the distal tip to a relatively straight shape.

In conventional guide wires, the very distal tip has a shaping ribbon acting as a shapeable tip that can be finger bent or kinked. The shaping ribbon or shapeable tip is usually a discrete part that is made from a different material than the superelastic NiTi distal core. This material that can be permanently deformed is welded or soldered to the distal end of the guide wire core.

The kinked, bent or curved tip in the guide wire and similar bend in the guide catheter enable the cardiologist to guide the tip of the catheter during catheter advancement, which involves pushing and rotating the bent tip within the patient's vascular system. To rotate and steer the guide wire, the cardiologist manually twists the external proximal portion of the catheter guide wire. The bent tip further allows the cardiologist to clearly discern the distal tip of the guide wire under fluoroscopy. Accordingly, such angled or bent guide wires have been found to be very helpful to negotiate tortuous blood vessels with angled branches and varying diameters.

SUMMARY OF THE INVENTION

The present invention in various embodiments is directed to a guide wire for use in a medical procedure, comprising an elongated core including a superelastic nickel-titanium alloy at a distal end, the distal end of the elongated core having a tapered section leading to a shapeable distal tip. A flexible body is disposed at the distal end. A polymer coating covers at least a portion of the elongated core. The shapeable tip includes the nickel-titanium alloy and further includes permanent deformation from at least two different radial directions that serves to reduce or eliminate superelasticity so that subsequent plastic deformation to shape the tip can be achieved with finger pressure. This enables the cardiologist or operator in the cath lab to conveniently impart a permanent curve, bend, kink or J-shape therein.

Typical wires tend to have crystals with nearly identical orientation in the axial direction, and nearly random radial orientation. On the other hand, the preferred embodiment guide wire has a distal tip that includes strain hardening in multiple radial directions wherein the crystallographic texture has been modified in those radial directions to be ordered. The core includes a longitudinal axis and the radial directions are rotated about this axis. In one embodiment, the multiple radial directions are about 33° to about 45° apart, and more preferably about 90° apart.

The present invention is further directed to a process for modifying a guide wire for use in a medical procedure. The process contemplates drawing an elongated core including a nickel-titanium alloy at a distal end; grinding down the distal end of the elongated core to create a tapered section leading to a shapeable distal tip; coating the elongated core at least partially with a polymer coating; strain hardening the shapeable tip having superelastic nickel-titanium alloy from a first radial direction to impart crystallographic texture aligned with the first radial direction and greatly reduce the superelasticity along the shapeable tip; rotating the core about its longitudinal axis; and strain hardening the shapeable tip having superelastic nickel-titanium alloy from a second radial direction to impart crystallographic texture aligned with the second radial direction and eliminate the superelasticity along the shapeable tip.

The steps of strain hardening the shapeable tip and rotating the core about its longitudinal axis are optionally repeated until the superelasticity along the shapeable distal tip is at least substantially eliminated so that the strain hardened shapeable tip can be plastically deformed with finger manipulation. Strain hardening can be accomplished by cold working the nitinol. The actual reduction in cross-section has been tested and is closer to 1%. The flattening is not of a change in profile, rather a reduction in area.

DETAILED DESCRIPTION OF THE PREFERRED EMBODIMENTS

The present invention in various preferred embodiments is directed to a guide wire for use in a medical procedure. The guide wire is preferably made from an elongated core having a superelastic nickel-titanium alloy section at the distal end. The distal end of the elongated core has a tapered section leading to a shapeable distal tip that is integral with and made from the same material as the nickel-titanium distal core section. As a result, the shapeable tip is also made from superelastic nickel-titanium, but undergoes permanent strain hardening from at least two different radial directions imparting crystallographic texture in those radial directions that limit superelasticity so that permanent deformation can be achieved with only finger pressure. A flexible body is disposed at the distal end and a polymer coating covers at least a portion of the elongated core. The proximal section of the guide wire core may be made from a medical device grade stainless steel or other metal that is joined to the nickel-titanium distal core section.

Crystallographic texture usually occurs in flow forming or deep drawing, say, of aluminum sheet metal for beer or soda cans. The flow forming or deep drawing causes all of the crystals that comprise the starting grain structure to be displaced and realigned. The deep drawn soda can tubular form with reoriented and generally aligned crystals tends to exhibit great strength in the axial direction and lesser strength in the radial direction.

Typical metal wires tend to have crystals with nearly identical orientation in the axial direction, and nearly random radial orientation. On the other hand, the preferred embodiment of the present invention guide wire has a distal tip made from a superelastic nickel-titanium alloy that has undergone strain hardening in multiple radial directions such that the crystallographic texture has been modified in those radial directions and are now ordered and generally aligned in those radial directions.

Once the crystallographic texture has been achieved at the distal tip, it becomes shapeable by hand and retains its shape. Thus, the operator may kink the distal tip or bend it into a J-shape as desired even though the material started as a superelastic nickel-titanium alloy.

Figure 1:
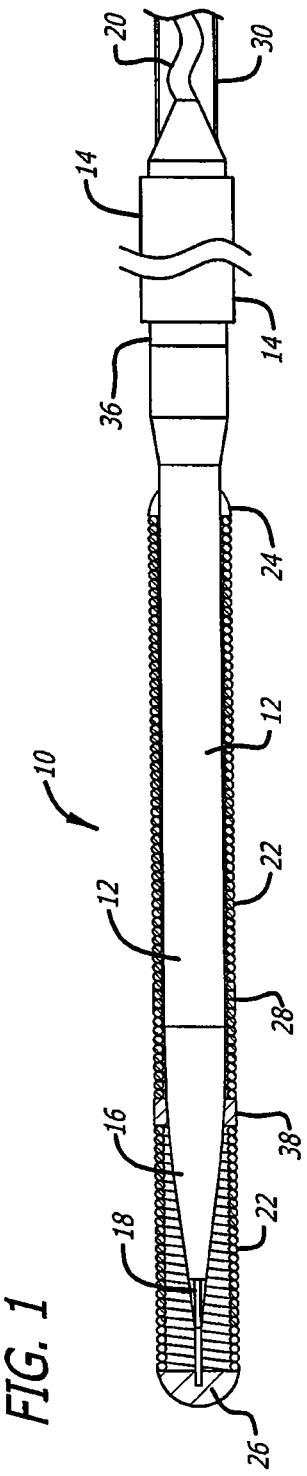
FIG. 1 is a side elevational view partially in section of a guide wire embodying features of the invention.

FIG. 1 is a simplified, schematic drawing of a preferred embodiment guide wire 10 employing the present invention. The guide wire 10 in the illustrated embodiment is made from a core section wherein the distal core section 12 is made from a highly elastic material such as superelastic nickel-titanium alloy (NiTi or nitinol) such as described in U.S. Pat. No. 5,341,818 (Abrams et al.), which is incorporated by reference herein. Other materials such as the high strength alloys described in U.S. Pat. No. 5,636,641 (Fariabi), also incorporated herein by reference, may be used. The distal core section may also be made from medical grade stainless steel. The proximal section 14 of the core is preferably made from a high strength metal such as 304V stainless steel.

The two core sections 12, 14 can be joined by a weld as shown, or by brazing, soldering, or adhesive bonding. In an alternative embodiment, the two sections may be joined by use of a hypotube covering the joint (not shown). The tapered section 16 of the distal core section 12 is preferably tapered and that tapered section 16 has preferably undergone a grind to create a parabolic profile, giving that segment of the core a linear increase in support as compared to a straight tapered profile. The extra support improves tip control when tracking through vasculature (not shown). At the very distal end of the tapered section is a cold worked and flattened superelastic distal tip 18 contemplated by the present invention.

At the proximal end, the stainless steel proximal core section 14 may extend all the way to the very proximal end (not shown), or may include an optional dock exchange hardware 20 for quickly changing out or extending the length of the proximal core section of the guide wire as desired, as shown in, for example, U.S. Pat. No. Re 34,466 (Taylor et al.) and U.S. Pat. No. 6,451,026 (Biagtan et al.), the contents of which are incorporated by reference. Optional informational markers 30 may be applied to the exterior of the dock extension 20.

At the distal core section 12 are one or more flexible bodies 22 made of one or more helical coiled springs. As seen in FIG. 1, the flexible bodies 22 overlie the distal core 12 and is preferably joined by adhesive (or solder alternatively) to the core at location 24 and at the very distal end via a solder ball or nose cone 26. The helical coil 22 is formed of a suitable radiopaque material such as platinum or alloys thereof or formed of other material such as stainless steel and coated with a radiopaque material such as gold. The wire from which the coil is made generally has a transverse diameter of about 0.002 inch (0.05 mm). The overall length of the coil 14 is typically comprised of about 3 cm for the distal tip coil and about 20-23 cm for the proximal coil. Multiple turns of the distal portion of coil 14 may be expanded to provide additional flexibility.

The tip coil or flexible bodies 22 may also be made from a radiopaque material or coated with such material. An optional radiopaque marker 28 may be positioned along the distal core section 12.

Typically, the overall length of the guide wire is about 190-195 cm, with a dock exchange length of about 300-305 cm. The first tapered segment is about 3 cm in length and the second tapered segment is about 4 cm in length. In a presently preferred embodiment, the guide wire 10 has a proximal core section 14 of about 0.014 inch (0.36 mm) in diameter, the first tapered core segment 16 has a diameter ranging from 0.014 inch down to about 0.008 inch (0.36-0.20 mm) and the second tapered core segment has a diameter ranging from about 0.007 to about 0.010 inch (0.178-0.254 mm). A flattened distal tip 18 extends from the distal end of the second tapered core segment 16 to the body of solder 26 which secures the distal tip 18 to the distal end of the helical coil 22. Another body of solder 38 secures the proximal end of the helical coil 22 to an intermediate location on the second tapered core segment 16.

The guide wire core 10 is preferably coated with a multilayer lubricious coating. In a preferred embodiment, the proximal core section 14 has a lubricious coating such as polytetrafluoroethylene (PTFE), with a single layer of a DOW®360 coating on top of that for lubricity. The base coat may be any of a variety of fluoropolymer coatings, e.g., TEFLON® available from DuPont, and which extends the length of the proximal core section 14. The distal core section 12 may be polyvinylpyrrolidone (PVP) hydrophilic coated entirely or optionally leaving the first 3 cm of the tip uncoated. The distal core section 12 may also be provided with a coating, such as a hydrophilic coating of the type known in the art. A hydrophilic coating is typically preferred on the distal portion of the wire, as it comes into contact with the arterial wall.

As seen in the FIG. 1 embodiment, the nickel-titanium distal core section 12 transitioned via the tapered section 16 into a shapeable tip 18, wherein the entire structure is made from superelastic nickel-titanium. However, it is preferable in this embodiment that the very distal 3 cm from the tip be cold worked as described to eliminate the superelasticity by hammering, rolling, and/or drawing in different radial directions thus imparting a crystallographic texture in those radial directions. The permanent cold work results in strain hardening that creates a linear elastic stress-strain profile so that the physician, cardiologist, or guide wire operator can easily and permanently kink, bend, or curve the tip 18 with finger pressure.

Figure 4:
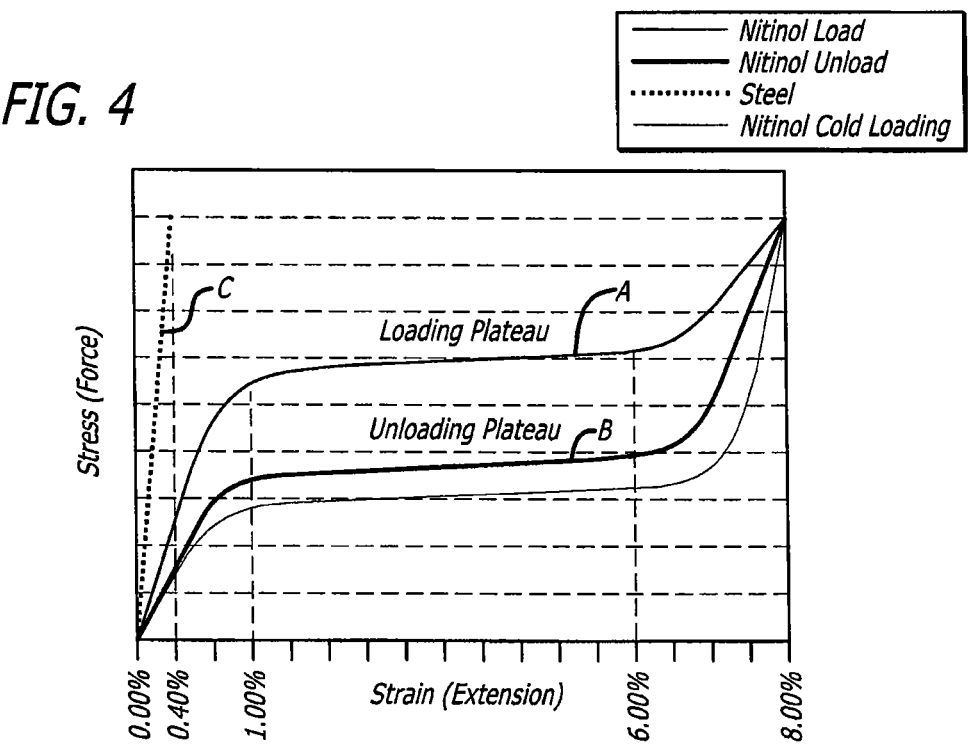
FIG. 4 is a stress-strain graph of a typical steel wire plotted against a typical nickel-titanium wire.

FIG. 4 is a representative graph of a typical stress-strain curve showing the idealized "flag" behavior of a binary nickel-titanium alloy under stress and when that stress is removed. The upper plateau of the flag curve represents the loading phase as identified by A, and curve B represents the unloading phase plateau. The A-B curve represents the behavior of nickel-titanium as compared to line C which is representative of common steel. Thus, superelastic nitinol is characterized by a linear section, then a long loading plateau and an upturn at the end, a downward slope and another plateau. The superelasticity occurs along the plateaus. The benefit of using superelastic nitinol over steel in a guide wire is the large amount of deformation that may be absorbed before taking a permanent set. A superelastic distal core section in a guide wire is highly kink resistant and atraumatic, especially when advanced through the tortuous vasculature of a patient. But the difficulty of using superelastic nitinol at the very distal tip of the core wire is that it cannot be shaped very easily. As explained earlier, a different material must be added to the superelastic distal tip of the core wire to allow the guide wire to be shaped.

Figure 5:
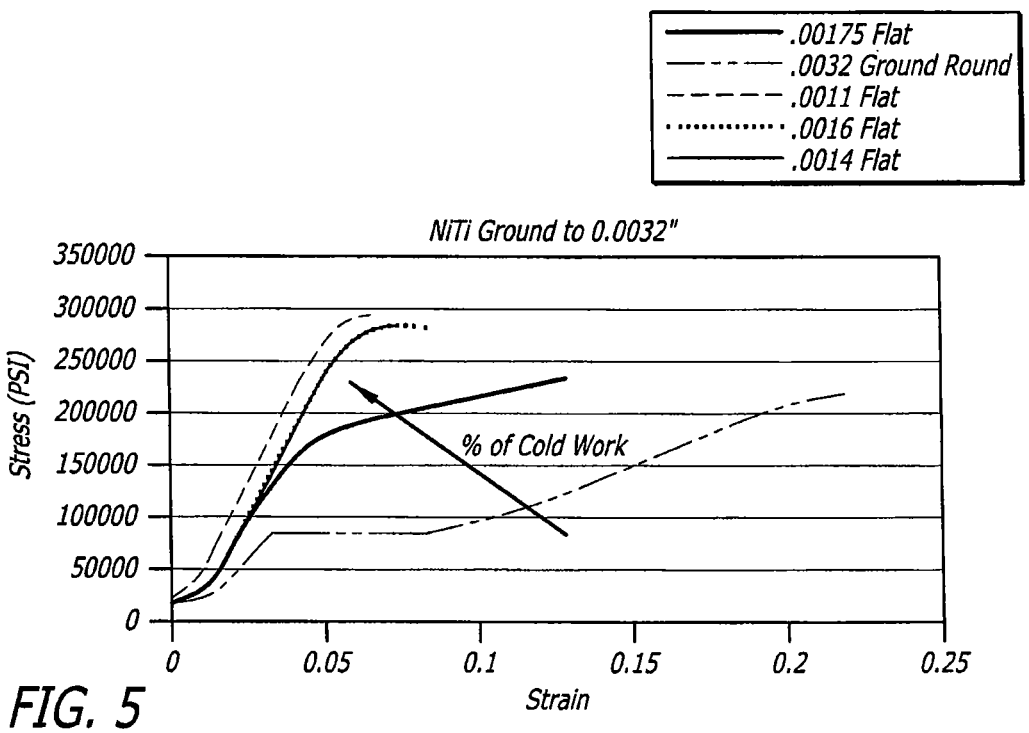
FIG. 5 is a stress-strain graph showing the effects of cold working according to the present invention to change the stress-strain characteristics of the alloy.

FIG. 5 is a stress-strain graph plotting the cold work imparted to the Ni—Ti wire to eliminate the superelastic behavior and arrive at a more linear elastic behavior as indicated by the upward diagonal arrow. The linear elastic stress-strain profile after the cold work allows that strain hardened portion of the NiTi wire to be easily shapeable or customized by finger pressure of a cardiologist or operator.

FIG. 5 is representative of the amount of cold working and permanent strain needed for typically binary nickel-titanium alloy in a 0.0032 wire stock. As depicted by the empirical numbers in the stress-strain graph, the amount of cold work is about 60% to 70%. Overall, as shown in FIG. 5, by imparting the strain indicated with cold work, the superelastic behavior of the nitinol is generally eliminated in favor of a linear elastic stress-strain profile.

Figure 6:
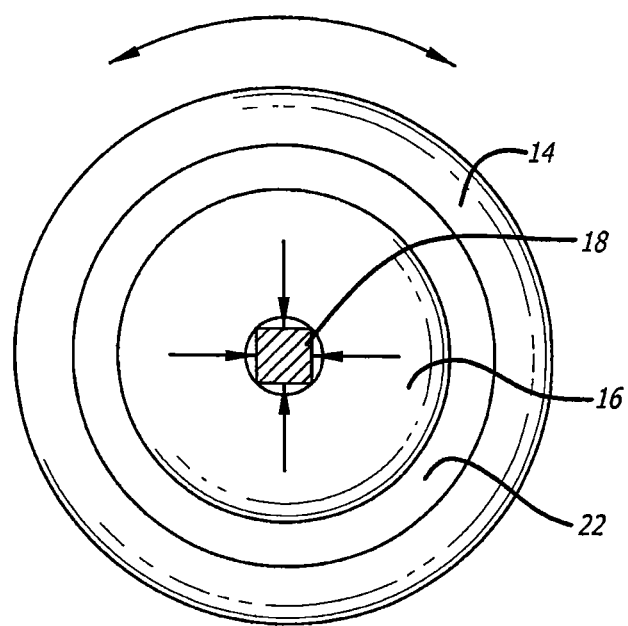
FIG. 6 is a cross-sectional view of the distal tapered segment of the guide wire to show the distal tip undergoing cold work from different radial directions.

By turning the guide wire core thus rotating the distal tip 18 about its longitudinal axis, as shown in FIG. 6, and then imparting the cold work to the distal tip 18 as shown in FIG. 6 along radial directions (indicated by the arrows), it is possible to create crystallographic textures in those radial directions which textures align and order the crystals. This texture then enables the formerly superelastic distal tip 18 to be easily and permanently shaped under finger pressure by the cardiologist or operator. The cross-sectional shape of the distal tip 18 in this embodiment is a square, having been rotated 90 degree at each application of cold work. Other polygonal shapes are possible such as a hexagon where the distal tip is rotated 60° at each application of cold work.

Figure 2:
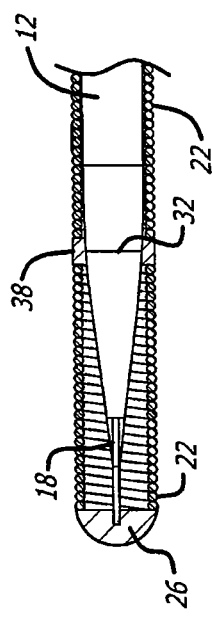
FIG. 2 is a side elevational view partially in section of an alternative embodiment of the distal tapered core section and shapeable tip.

In FIG. 2, an alternative distal end is shown wherein the first one centimeter or thereabouts from the distal end undergoes the flattening permanent strain operation to create a polygonal shaped cross-section while the more proximal section has a tapered profile, yet also exhibits the pseudoelastic behavior of strain-hardened nitinol. This section 18 is then welded at joint 32 to the distal core section 12.

Figure 3:
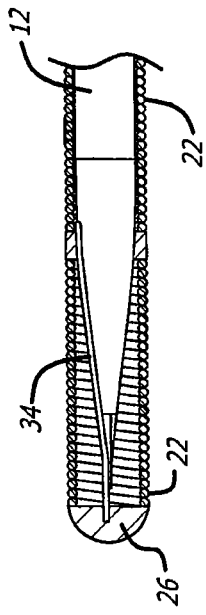
FIG. 3 is a side elevational view partially in section of another alternative embodiment of the distal tapered core section and shapeable tip.

In FIG. 3, there is shown yet another alternative embodiment distal end wherein the tapered distal section 16 is untouched and remains superelastic, but a linear elastic nitinol shaping ribbon 34 is welded or otherwise joined to the distal core section 12. The shaping ribbon 34 has undergone the radial cold working operation to change the formerly superelastic nitinol into a linear elastic metal via the described radial cold working steps.

The stainless steel to nickel titanium weld at location 36 may be accomplished according to techniques disclosed in, for example, U.S. Pat. No. 6,702,762 (Jafari et al.) and U.S.

Patent Application Publication No. 2006/0047223 A1 (Grandfield et al.), all of whose contents are hereby incorporated by reference.

The distal end of the guide wire core 10 may be pre-tinned specifically at the superelastic NiTi distal core section 12 including the tapered distal section 16. The pre-tinning includes applying a gold-tin coating over the cold worked NiTi core sections. The distal core sections 12, 16 then undergo the cold work processing described above. The cold work processing steps do not damage the pre-tin coating, and the pre-tinning step does not impart unwanted heat treat to the NiTi core which cold detrimentally affect its superelastic behavior. The cold work may alternatively be performed first, but the pre-tinning step may undo the strain hardening of the cold work. Customization of the distal section 16 with the pre-tinning can be achieved with low finger force and the customized section, whether a kink, bend, curve, J-shape, etc., will hold its shape. Also, the pre-tinning step with the gold-tin coating allows easier tip coil attachment to the nitinol core via the conventional silver solder used for this purpose.

It is to be understood that the foregoing description is intended to be illustrative of embodiments of the present invention but is not intended to be limiting in any manner. One of ordinary skill in the art will readily appreciate modifications and alterations to the above described examples, and the intention includes all such modifications and alterations. Accordingly, the scope of the invention is properly interpreted to be encompassed by the words of the appended claims, using their ordinary meaning, without limiting the definition of those words to the examples provided herein.

What is claimed:

1. A process for modifying a guide wire for use in a medical procedure, comprising:
    cold working a binary nickel-titanium alloy wire by hammering, rolling and/or drawing in different radial directions in a range from 60% to 70% thereby imparting a crystallographic texture in the radial directions to create a linear elastic stress-strain profile in the guide wire.

2. The guide wire of claim 1, wherein the wire is comprised of a 0.0032 inch wire stock.

3. The guide wire of claim 1, wherein prior to cold working the wire, a distal section of the wire is pre-tinned.

4. The guide wire of claim 3, wherein the pre-tinning includes application of a gold-tin coating on the distal section.

5. The guide wire of claim 1, wherein during the cold working process, a distal tip of the guide wire is rotated about a longitudinal axis.

6. The guide wire of claim 5, wherein the cold working is imparted to the distal tip in radial directions in order to create the crystallographic textures in the radial directions which textures align and order the crystals.

7. The guide wire of claim 6, wherein the distal tip is rotated 90° at each application of cold work.

* * * * *